(12) United States Patent
Maurin et al.

(10) Patent No.: US 6,538,011 B1
(45) Date of Patent: Mar. 25, 2003

(54) COMPOSITION FOR THE ANTIDANDRUFF TREATMENT OF THE HAIR AND SCALP BASED ON AN ANTIDANDRUFF ACTIVE PRINCIPLE AND ON A HYDROXY ACID

(75) Inventors: Véronique Maurin, Paris (FR); Bernard Beauquey, Clichy (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 09/612,922

(22) Filed: Jul. 10, 2000

(30) Foreign Application Priority Data

Jul. 8, 1999 (FR) .............................. 99 08877

(51) Int. Cl.⁷ ...................... A61K 31/44; A61K 31/19; A61K 7/075
(52) U.S. Cl. ...................... 514/345; 514/287; 514/301; 514/574; 514/570; 514/558; 514/553; 514/880; 514/881; 424/70.31
(58) Field of Search ................. 514/345, 287, 514/301, 574, 570, 558, 553, 880, 881; 424/70.31

(56) References Cited

U.S. PATENT DOCUMENTS

| | | |
|---|---|---|
| 2,528,378 A | 10/1950 | Mannheimer |
| 2,781,354 A | 2/1957 | Mannheimer |
| 3,753,916 A | 8/1973 | Parran |
| 4,345,080 A | 8/1982 | Bolich, Jr. |
| 5,037,818 A | 8/1991 | Sime |
| 5,886,031 A * | 3/1999 | Shin et al. .................. 514/478 |

FOREIGN PATENT DOCUMENTS

| | | |
|---|---|---|
| EP | 0 273 202 | 7/1988 |
| EP | 0 413 528 | 2/1991 |
| EP | 0 422 508 | 4/1991 |
| GB | 2 180 946 | 4/1987 |
| WO | 98/46203 | * 10/1998 |
| WO | 98/55093 | 12/1998 |

OTHER PUBLICATIONS

CA132L171116, Niemiec et al, WO 2000007627, abstract, Feb. 17, 2000.*
CA129:3354721, Turowski–Wanke et al, WO 9846203, abstract, Oct. 22, 1998.*
CA121:308342, Hirota et al, JP 06234618, abstract, Aug. 23, 1994.*
CA120:253066, Takahashi et al, JP 05310541, abstract, Nov. 22, 1993.*
CA108:101371, Smith et al., GB 2187197, abstract, Sep. 3, 1987.*
CA108:192594, Smith et al, EP217635, abstract, Apr. 8, 1987.*
Database Chemical Abstracts, XP002131948, JP 06 234618, Aug. 23, 1994.

* cited by examiner

*Primary Examiner*—Rebecca Cook
(74) *Attorney, Agent, or Firm*—Finnegan, Henderson, Farabow, Garrett & Dunner, L.L.P.

(57) ABSTRACT

Cosmetic or dermatological compositions for washing and/or antidandruff treatment of hair and/or scalp comprising at least one antidandruff agent chosen from pyridinethione salts, at least 1% by weight of at least one hydroxy acid, and at least one amphoteric surface-active agent or nonionic surface-active agent of the alkyl(poly)glycoside type.

27 Claims, No Drawings

COMPOSITION FOR THE ANTIDANDRUFF TREATMENT OF THE HAIR AND SCALP BASED ON AN ANTIDANDRUFF ACTIVE PRINCIPLE AND ON A HYDROXY ACID

The present invention relates to cosmetic compositions for the washing and the antidandruff treatment of the hair and scalp based on an antidandruff agent, a hydroxy acid and an amphoteric or nonionic surface-active agent of the alkyl (poly)glycoside type.

For combatting the formation of dandruff, generally accompanied by microbial and/or fungal proliferation, provision has been made, as antidandruff products either for products that inhibit microbial proliferation or for keratolytic products. The use of pyrithione salts has been recommended among these antidandruff agents. Numerous patents disclose pyridinethione salts in shampoos, for example U.S. Pat. Nos. 3,753,916, 4,345,080 and 5,037,818. The surfactants used in the shampoos are generally anionic surfactants.

Provision has also been made, in European published application EP-A-0,422,508, for the use in shampoos of antibacterial agents, such as pyridinethione salts, in combination with a nonionic surface-active agent of the alkylpolyglucoside type.

However, the inventors have found that these shampoos exhibit a still insufficient antifungal activity, in particular, with respect to Malassezia ovalis. Furthermore, as pyridinethione salts are insoluble in water, they can also present suspending problems if present at relatively high levels.

It has now been found, surprisingly and unexpectedly, that it is possible to obtain compositions, in particular, cosmetic compositions, for the washing and the antidandruff treatment of the hair and scalp that can exhibit an improved antidandruff effectiveness by combining at least one antidandruff agent of the pyridinethione type, at least 1% by weight of a hydroxy acid, and at least one surface-active agent chosen from nonionic surfactants of the alkyl(poly) glycoside type and amphoteric surfactants.

A subject of the invention is therefore a composition for the washing and the antidandruff treatment of the hair and scalp comprising, typically in an aqueous medium, at least one antidandruff agent chosen from pyridinethione salts, at least 1% by weight of at least one hydroxy acid, and at least one surface-active agent chosen from nonionic surfactants of the alkyl(poly)glycoside type and amphoteric surfactants.

Another subject of the invention comprises a washing and cosmetic treatment process for removing dandruff from the hair or scalp using these compositions.

Other subjects will become apparent in light of the description and examples that follow.

The pyridinethione salts are chosen, generally, from calcium, magnesium, barium, strontium, zinc, cadmium, tin and zirconium salts. The zinc salt is used in one embodiment.

Such compounds are sold under the name Zinc omadine by the company Olin.

The pyridinethione salt or salts are present in the compositions according to the invention in proportions generally ranging from 0.1 to 5% by weight and, in some embodiments, from 0.3 to 2.5% by weight, with respect to the total weight of the composition.

The detergent compositions according to the invention comprise at least 1% by weight of a hydroxy acid or of its derivatives.

The term "acid derivatives" used with a term is understood to mean its associative salts (salts with an organic base or an alkaline substance, in particular) or alternatively, optionally, its corresponding lactide (form obtained by self-esterification of the molecules).

The hydroxy acid can, of course, comprise a mono- or polycarboxylic acid comprising one or more hydroxyl functional groups; the hydroxy acid can be an α-hydroxy acid, at least one of these hydroxyl functional groups having to occupy an α-position on the acid (carbon adjacent to a carboxyl functional group). This acid can be provided in the final detergent composition in the form of the free acid and/or in the form of one of its associative salts (for example, salts with an organic base or an alkaline substance), notably according to the final pH imposed on the composition, or alternatively, optionally, in the form of the corresponding lactide (form obtained by self-esterification of the molecules). The detergent compositions according to the invention can, of course, comprise one or more hydroxy acids or their derivatives.

Examples of such compounds include, inter alia, citric, lactic, methyllactic, phenyllactic, malic, mandelic, glycolic, .tartronic, tartaric, gluconic, benzylic and 2-hydroxycaprylic acids. Other compounds of the hydroxy acid type suitable in the present invention are those cited in European Patent Application EP-A-0,413,528, the disclosure of which is incorporated by reference herein. Use can be made of the acids that are cosmetically compatible and acceptable with the hair, skin and/or scalp.

According to one embodiment of the present invention, the hydroxy acid employed is chosen from citric acid, tartaric acid and lactic acid.

In another aspect of the detergent compositions according to the invention, the hydroxy acid or acids are present in the latter in a proportion of at least 1% by weight, and in some embodiments at least 2% by weight, with respect to the whole composition. Hydroxy acid content can range from 2 to 10% by weight and, in some embodiments, from 2 to 5% by weight. It should be noted that these concentrations are markedly greater than those which may sometimes be encountered in shampoos not of the invention when some acids were employed solely for the purposes of adjusting the pH.

The nonionic surface-active agent or agents of alkyl (poly)glycoside type used in the context of the present invention are well-known products including those represented by the following general formula (I):

$$R_1\text{—O—}(R_2O)_t\text{—}(G)_v \qquad (1)$$

in which

R$_1$ represents a saturated or unsaturated, linear or branched alkyl radical comprising approximately from 8 to 24 carbon atoms or an alkylphenyl radical in which the linear or branched alkyl radical comprises approximately from 8 to 24 carbon atoms, R$_2$ represents an alkylene radical comprising from 2 to 4 carbon atoms, G represents a reduced sugar comprising from 5 to 6 carbon atoms, t denotes a value ranging from 0 to 10 and v denotes a value ranging from 1 to 15.

Alkyl(poly)glycosides according to the present invention can be compounds of formula (I) in which R$_1$ is chosen from a saturated or unsaturated, linear or branched alkyl radical comprising from 8 to 14 carbon atoms, t denotes a value ranging from 0 to 3 and in some embodiments is equal to 0, and G denotes glucose, fructose or galactose. The degree of polymerization (S) of the saccharide, i.e., the value of v in the formula (I), can range from 1 to 15. According to the invention, preference is given to reduced sugars comprising 80% or more of sugars where the degree of polymerization (S) has a value ranging from 1 to 4. The mean degree of polymerization generally ranges from 1 to 2.

Compounds of formula (I) generally are represented by the products sold by the company Henkel under the name APG, such as the products APG 300, APG 350, APG 500, APG 550, APG 625 or APG base 10–12, or under the names PLANTAREN® (1200 and 2000) or PLANTACARE® (818, 1200 and 2000). Use may also be made of the products sold by the company Seppic under the names Triton CG 110 (or Oramix CG 110) and Triton CG 312 (or ORAMIX® NS 10), the products sold by the company BASF under the name Lutensol GD 70 or those sold by the company Chem Y under the name AG10 LK.

The amphoteric surface-active agents can be (non-limiting list) aliphatic secondary or tertiary amine derivatives, in which the aliphatic radical is a linear or branched chain comprising from 8 to 22 carbon atoms which comprises at least one water-solubilizing anionic group, for example, carboxylate, sulphonate, sulphate, phosphate or phosphonate; mention may also be made of ($C_8$–$C_{20}$)alkyl betaines, sulphobetaines, ($C_8$–$C_{20}$)alkyl amido($C_1$–$C_6$)alkyl betaines and ($C_8$–$C_{20}$)alkyl amido($C_1$–$C_6$)alkyl sulphobetaines.

Mention may be made, among amine derivatives, of the products sold under the name Miranol, as disclosed in U.S. Pat. Nos. 2,528,378 and 2,781,354, the disclosure of each of which is incorporated by reference herein, and with structures:

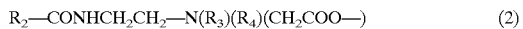

$$R_2\text{—CONHCH}_2\text{CH}_2\text{—N}(R_3)(R_4)(CH_2COO\text{—}) \quad (2)$$

in which:
$R_2$ denotes an alkyl radical derived from an $R_2$—COOH acid present in hydrolysed coconut oil or a heptyl, nonyl or undecyl radical, $R_3$ denotes a β-hydroxyethyl group and $R_4$ denotes a carboxymethyl group; and

$$R_5\text{—CONHCH}_2\text{CH}_2\text{—N}(B)(C) \quad (3)$$

in which:
(B) represents —$CH_2CH_2OX'$, (C) represents —$(CH_2)_z$—Y', with z=1 or 2,
X' denotes the —$CH_2CH_2$—COOH group or a hydrogen atom,
Y' denotes —COOH or the —$CH_2$—CHOH—$SO_3H$ radical, and
$R_5$ denotes an alkyl radical of a carboxylic acid present in hydrolysed linseed oil or coconut oil, an alkyl radical, such as a $C_7$, $C_9$, $C_{11}$, or $C_{13}$ alkyl radical, a $C_{17}$ alkyl radical and its iso form, or an unsaturated $C_{17}$ radical.

These compounds are classified in the CTFA dictionary, 7th edition, 1997, under the names Disodium Cocoamphodiacetate, Disodium Lauroamphodiacetate, Disodium Capryloamphodiacetate, Disodium Caproamphodiacetate, Disodium Cocoamphodipropionate, Disodium Lauroamphodipropionate, Disodium Caproamphodipropionate, Disodium Caprylo-amphodipropionate, Lauroamphodipropionic acid, and Cocoamphodipropionic acid. Mention may be made, as an example, of the disodium cocoamphodiacetate sold under the tradename Miranol7 C2M concentrate by the company Rhodia Chimie.

According to the present invention, it is possible to use the amphoteric surface-active agents belonging to the group of betaines, such as the alkyl betaines, for example, the cocoyl betaine sold under the name "DEHYTON® AB 30" as a 30% aqueous solution of AM by the company Henkel, or the ($C_8$–$C_{20}$)alkyl amido($C_1$–$C_6$)alkyl betaines, for example, TEGOBETAINE® F50, sold by the company Goldschmidt.

The amphoteric or nonionic surface-active agent(s) are generally present in an amount ranging from approximately 0.5 to approximately 15% by weight, and in some embodiments from 1 to 5% by weight, with respect to the total weight of the composition.

The compositions of the invention can advantageously comprise, in addition, at least one other surface-active agent generally present in an amount ranging from 0.1% to 40% by weight approximately, some embodiments comprise from 3% to 30% and, other embodiments comprise from 5% to 20%, with respect to the total weight of the composition.

This surface-active agent is generally chosen from anionic surface-active agents.

The additional anionic surfactants suitable for the implementation of the present invention, include the following examples: anionic surfactants, alone or as mixtures of (non-limiting list) the salts, for example, alkali metal salts, especially sodium salts, ammonium salts, amine salts, aminoalcohol salts or magnesium salts, of the following compounds: alkyl sulphates, alkyl ether sulphates, alkylamido ether sulphates, alkylaryl polyether sulphates or monoglyceride sulphates; alkylsulphonates, alkyl phosphates, alkylamidesulphonates, alkylarylsulphonates, α-olefinsulphonates or paraffin-sulphonates; alkyl sulphosuccinates, alkyl ether sulphosuccinates or alkyl amide sulphosuccinates; alkyl sulphosuccinamates; alkyl sulphoacetates; alkyl ether phosphates; acylsarcosinates; acylisethionates and N-acyltaurates, the alkyl or acyl radical of all these various compounds may comprise from 8 to 24 carbon atoms and the aryl radical may denote a phenyl or benzyl group. Other examples include the anionic surfactants of the salts of fatty acids, such as the salts of oleic, ricinoleic, palmitic, stearic, coconut oil or hydrogenated coconut oil acids; or acyllactylates, the acyl radical of which comprises 8 to 20 carbon atoms. Use may also be made of weakly anionic surfactants, such as alkyl-D-galactosiduronic acids and their salts, as well as polyoxyalkylenated($C_6$–$C_{24}$)alkyl ether carboxylic acids, polyoxyalkylenated ($C_6$–$C_{24}$)alkylaryl ether carboxylic acids, polyoxyalkylenated($C_6$–$C_{24}$)alkylamido ether carboxylic acids and their salts, such as, for example, those comprising from 2 to 50 ethylene oxide groups, and their mixtures.

Preference is given, among anionic surfactants, to the use according to the invention of alkyl sulphate and alkyl ether sulphate salts and their mixtures.

The amount and the quality of the surfactants are those sufficient to confer a satisfactory foaming and/or detergent power on the final composition.

In the composition according to the present invention, the combined detergent surfactants are generally present in an amount ranging from 4 to 50% by weight and in some embodiments from 6 to 35% by weight, and in other embodiments from 8 to 25% by weight, with respect to the total weight of the composition.

The cosmetic compositions according to the invention can be provided in the form of more or less thickened liquids, of gels, of creams or of aerosol foams.

The cosmetically acceptable aqueous medium can be composed solely of water or of a mixture of water and of a cosmetically acceptable solvent, such as a lower $C_1$–$C_4$ alcohol, such as ethanol, isopropanoi, tert-butanol or n-butanol; alkylene glycols, such as propylene glycol, or glycol ethers.

The detergent compositions according to the invention exhibit a final pH generally ranging from 3 to 10. This pH can range from 4 to 9 in some embodiments. The pH can be conventionally adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or by addition of an inorganic or organic acid, such as a carboxylic acid.

The compositions according to the invention can comprise viscosity-regulating agents, such as electrolytes, or thickening agents, in addition to the combination defined above. Examples include sodium chloride, sodium xylenesulphonate, scleroglucans, xanthan gums, fatty acid alkanolamides, alkyl ether carboxylic acid alkanolamides optionally oxyethylenated with up to 5 mol of ethylene oxide, such as the product sold under the name "Aminol A15" by the company Chem Y, crosslinked polyacrylic acids and crosslinked acrylic acid/$C_{10}$–$C_{30}$ alkyl acrylate copolymers. These viscosity-regulating agents are used in the compositions according to the invention in amounts ranging up to 10% by weight with respect to the total weight of the composition.

The compositions according to the invention can also comprise up to 5% of pearlescent or opacifying agents well known in the art, such as, for example, fatty alcohols higher than $C_{16}$, sodium palmitate, magnesium palmitate, sodium stearate, sodium hydroxystearate, magnesium stearate, magnesium hydroxystearate, acylated derivatives comprising a fatty chain, such as ethylene glycol monostearate, ethylene glycol distearate, polyethylene glycol monostearate or polyethylene glycol distearate, or ethers comprising fatty chains, such as, for example, distearyl ether or 1-(hexadecyloxy)-2-octadecanol.

The detergent compositions according to the invention can, of course, in addition, comprise any of the usual adjuvants encountered in the field of shampoos, such as, for example, fragrances, preservatives, sequestering agents, thickeners, softeners, foam modifiers, colorants, moisturizing agents, other antidandruff or antiseborrhoeic agents, sunscreens and others.

The compositions according to the invention can optionally comprise, in addition, other agents having the effect of improving the cosmetic properties of the hair or skin, without, however, substantially detrimentally affecting the stability of the compositions. Mention may be made, in this respect, of cationic surface-active agents, anionic or nonionic or amphoteric or cationic polymers, proteins, protein hydrolysates, natural or synthetic waxes, ceramides, pseudoceramides, fatty acids comprising linear or branched $C_{16}$–$C_{40}$ chains, such as 18-methyleicosanoic acid, carboxylic acid fatty esters, fatty acid mono-, di- or triglycerides, vitamins, provitamins, such as panthenol, volatile or nonvolatile silicones which are soluble and insoluble in the medium, vegetable oils, synthetic oils, such as poly(α-olefins), fluorinated or perfluorinated oils, and their mixtures.

The compositions according to the invention can comprise, in some embodiments, at least one cationic polymer and/or one silicone.

Use can be made, among the cationic polymers which can be used in the context of the present invention, of quaternary cellulose ether derivatives, such as the products sold under the name "JR 400" by the company Union Carbide Corporation, cyclopolymers, such as the polymers or copolymers of dimethyldiallylammonium chloride and of acrylamide sold under the names "Merquat 100", "Merquat 550" and "Merquat S" by the company Calgon, cationic polysaccharides, such as the guar gums modified by 2,3-epoxypropyltrimethylammonium chloride sold for example under the name "Jaguar C13S" by the company Meyhall, and vinylpyrrolidone/methacrylamidopropyldimethylamine copolymers, sold, in particular, under the name Styleze CC 10 by the company ISP, and their mixtures.

According to the invention, the cationic polymer or polymers can be present in an amount ranging from 0.01% to 10% by weight of the total weight of the composition. In some embodiments it can be present in an amount ranging from 0.05% to 5% by weight and, in other embodiments, from 0.1 % to 3% by weight of the total weight of the final composition.

The compositions according to the invention can also comprise foam synergists, such as $C_{10}$–$C_{18}$ 1,2-alkanediols or fatty alkanolamides derived from mono- or from diethanolamine.

Of course, a person skilled in the art will take care to choose this or these optional additonal compounds and/or their amounts so that the advantageous properties intrinsically attached to the combination according to the invention are not, or not substantially, detrimentally affected by the envisaged addition or additions.

The additives are generally present in the compositions according to the invention in an amount ranging from 0.01% to 20% by weight, and can be present in an amount ranging from 0.02% to 10% by weight with respect to the total weight of the composition.

The compositions according to the invention are often used as shampoos for washing and treating the hair and scalp and they are applied, in that case, to wet or dry hair in amounts effective in washing it, this application being followed by rinsing, for example with water, after an optional period of standing.

Another subject of the invention is a cosmetic treatment process comprising applying to the hair, or to the scalp, a composition as defined above, this application being followed by rinsing, for example with water, after an optional period of standing.

The present invention is further illustrated by the following examples which are designed to teach those of ordinary skill in the art how to practice the invention. The following examples are merely illustrative of the invention and should not be construed as limiting the invention as claimed.

EXAMPLE 1

A shampoo was prepared with the following composition

| | |
|---|---|
| Sodium lauryl ether sulphate (2.2 EO) | 12.6 g AM |
| Sodium N-cocoylamidoethyl-N-(ethoxycarboxy-methyl)glycinate (Miranol C2M Conc NP from Rhodia Chimie) | 0.76 g AM |
| Cocoylbetaine (Dehyton AB30 from Goldschmidt) | 1.2 g AM |
| Zinc pyrithione, as an aqueous suspension comprising 48% of AM | 0.96 g AM |
| Citric acid | 3 g |
| Hydroxyethyl cellulose cross linked by epichlorohydrin and quaternized by triethylamine (JR400 from Union Carbide) | 0.25 g |
| Ethylene glycol distearate | 2 g |
| Cross linked poly(acrylic acid) | 0.3 g AM |
| Preservatives, fragrance | q.s. |
| pH adjusted to 5.5 | 5.5 |
| Water q.s. for | 100 g |

After having moistened the hair, a sufficient amount of the shampoo was applied, was then caused to foam and was allowed to stand for approximately 2 min. The hair was subsequently copiously rinsed. This shampoo, used regularly, made it possible to remove and to prevent the reappearance of dandruff.

Determination of the Fungistatic Activity

The fungistatic activity of the compositions A to D was determined by a conventional so-called MIC (Minimum Inhibitory Concentration) method, the MIC corresponding to the lowest concentration at which a given product inhibits the growth of a given strain under defined conditions. In this case, strains of *Malassezia ovalis* (or *Pityrospotum ovale*) CIP 1363.82 were used.

The determination of the fungistatic activity of the products was therefore carried out by the method of dilutions in agar-comprising medium. 100 µl of product were added to 1.9 ml of supercooled agar-comprising culture medium at 45° C. Successive dilutions, in geometric progression in a proportion of 2, of the suspension obtained were carried out using the supercooled agar-comprising culture medium in the wells of a plate (Falcon, 24 wells). After solidification of the medium, 4 µl of the microbial suspension were deposited at the surface using a micro pipette. After incubating for 48 h at 30° C., the minimum inhibitory concentration (M.I.C.) was given by the lowest concentration of product which inhibited microbial growth. The concentration of the antimicrobial agent from which the growth of the microorganism was completely inhibited (absence of clouding in the medium) was thus determined and expressed as a dilution. The results are collated in the following table:

|  | A Invention | B Invention | C | D | E Invention |
|---|---|---|---|---|---|
| Zn pyrithione | 0.96 g AM | 0.96 g AM | 0.96 g AM | — | 0.96 g AM |
| Citric acid | 3 g | 3 g | 3 g | — | 3 g |
| Cocoyl betaine (Dehython AB 30) | 13.8 g AM | — | — | 1.2 g AM | 1.2 g AM |
| APG (KAG 40 from KAO) | — | 13.8 g AM | — | — | — |
| Sodium lauryl ether sulphate (2.2 EO) | — | — | 13.8 g AM | 12.6 g AM | 12.6 g AM |
| Na sulphosuccinate | — | — | — | — | — |
| Water q.s. for | 100 g | 100 g | 100 g | 100 g | 100 g |
| MIC | 1/2560 | 1/2560 | 1/1280 | 1/80 | 1/2560 |

The lower the MIC, the more effective the composition.

The foregoing written description relates to various embodiments of the present invention. Numerous changes and modifications may be made therein without departing from the spirit and scope of the invention as defined in the following claims.

What is claimed is:

1. A cosmetic composition for washing and/or antidandruff treatment of hair and scalp, comprising:
    a) at least one antidandruff agent chosen from pyridinethione salts;
    b) at least one surface-active agent chosen from nonionic surfactants of the alkyl(poly)glycoside type; and
    c) at least 1% by weight of at least one hydroxy acid.

2. A composition according to claim 1, wherein said composition further comprises an aqueous medium.

3. A composition according to claim 1, wherein said pyridinethione salts are chosen from calcium, magnesium, barium, strontium, zinc, cadmium, tin and zirconium salts.

4. A composition according to claim 3, wherein said at least one antidandruff agent is the zinc salt of pyridinethione.

5. A composition according to claim 1, wherein said at least one antidandruff agent is present in an amount ranging from 0.1 to 5% by weight, with respect to the total weight of the composition.

6. A composition according to claim 1, wherein said at least one hydroxy acid is present in the form of a free acid, the form of one of its associative salts, or the form of its corresponding lactide.

7. A composition according to claim 1, wherein said at least one hydroxy acid is chosen from citric, lactic, methyllactic, phenyllactic, malic, mandelic, glycolic, tartronic, tartaric, gluconic, benzylic and 2-hydroxycaprylic acids.

8. A composition according to claim 1, wherein said at least one hydroxy acid is present in an amount ranging from 2 to 10% by weight, with respect to the total weight of the composition.

9. A composition according to claim 1, wherein said nonionic surface-active agents of the alkyl(poly)glycoside type comprise compounds of formula (I):

$$R_1\text{—}O\text{—}(R_2O)_t\text{—}(G)_v \qquad (I)$$

in which
R$_1$ is chosen from a saturated or unsaturated, linear or branched alkyl radical comprising from 8 to 24 carbon atoms and an alkylphenyl radical in which the linear or branched alkyl radical comprises from 8 to 24 carbon atoms; R$_2$ is an alkylene radical comprising from 2 to 4 carbon atoms; G is a reduced sugar comprising from 5 to 6 carbon atoms; t is a value ranging from 0 to 10; and v is a value ranging from 1 to 15.

10. A composition according to claim 9, wherein in said formula (I), R$_1$ is chosen from a saturated or unsaturated, linear or branched alkyl radical comprising from 8 to 14 carbon atoms, t is 0, G is glucose, and v ranges from 1 to 4.

11. A composition according to claim 1, wherein said at least one surface-active agent is present in an amount ranging from 0.5 to 15% by weight, with respect to the total weight of the composition.

12. A composition according to claim 1, further comprising at least one anionic surface-active agent.

13. A composition according to claim 12, wherein said at least one anionic surface-active agent is present in an amount ranging from 0.1% to 40% by weight approximately, with respect to the total weight of the composition.

14. A composition according to claim 13, wherein said at least one anionic surface-active agent is present in an amount ranging from 3% to 30% by weight approximately, with respect to the total weight of the composition.

15. A composition according to claim 1, further comprising at least one additive chosen from cationic surface-active agents, anionic, nonionic, amphoteric and cationic polymers, proteins, protein hydrolysates, natural and synthetic waxes, ceramides, pseudoceramides, fatty acids comprising linear $C_{16}$–$C_{40}$ chains and fatty acids comprising branched $C_{16}$–$C_{40}$ chains, carboxylic acid fatty esters, fatty acid mono-, di- and triglycerides, vitamins, provitamins, volatile and nonvolatile silicones which are soluble in the composition, volatile and nonvolatile silicones which are insoluble in the composition, vegetable oils, synthetic oils, fluorinated oils, and perfluorinated oils.

16. A composition according to claim 15, wherein said at least one additive is 18-methyleicosanoic acid.

17. A composition according to claim 15, wherein said at least one additive is panthenol.

18. A composition according to claim 15, wherein said synthetic oils are chosen from poly($\alpha$-olefins).

19. A composition according to claim 15, wherein said cationic polymers are chosen from quaternary cellulose ether derivatives, cyclopolymers, cationic polysaccharides, vinylpyrrolidone/methacrylamidopropyldimethylamine copolymers and their mixtures.

20. A composition according to claim 15, wherein said at least one additive chosen from cationic polymers is present in an amount ranging from 0.01% and 10% by weight with respect to the total weight of the composition.

21. A composition according to claim 20, wherein said at least one additive chosen from cationic polymers is present in an amount ranging from 0.05% and 5% by weight with respect to the total weight of the composition.

22. A composition according to claim 1, wherein said composition has a pH ranging from 4 to 9.

23. A method for washing and/or treating the hair and/or scalp, said method comprising applying to the hair and/or scalp at least one composition which comprises:
   a) at least one antidandruff agent chosen from pyridinethione salts;
   b) at least one surface-active agent chosen from nonionic surfactants of the alkyl(poly)glycoside type; and
   c) at least 1% by weight of at least one hydroxy acid.

24. A method according to claim 23, wherein said treatment is an antidandruff treatment.

25. A cosmetic or dermatological treatment method, said method comprising applying to the hair and/or scalp at least one composition which comprises:
   a) at least one antidandruff agent chosen from pyridinethione salts;
   b) at least one surface-active agent chosen from nonionic surfactants of the alkyl(poly)glycoside type; and
   c) at least 1% by weight of at least one hydroxy acid, and rinsing the hair and/or scalp.

26. A method according to claim 25, wherein before said rinsing and after said applying, said composition is allowed to stand on said hair and/or scalp.

27. A method according to claim 25, wherein said rinsing is performed with water.

\* \* \* \* \*